(12) United States Patent
Lai

(10) Patent No.: US 6,786,899 B1
(45) Date of Patent: *Sep. 7, 2004

(54) EYE TRACKING EMPLOYING A RETRO-REFLECTIVE DISK

(76) Inventor: Ming Lai, 6450 Dougherty Rd., #125, Dublin, CA (US) 94568

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/356,474

(22) Filed: Jul. 19, 1999

Related U.S. Application Data

(60) Provisional application No. 60/093,618, filed on Jul. 21, 1998.

(51) Int. Cl.[7] .................................................. A61F 9/007
(52) U.S. Cl. .................................. 606/4; 606/5; 606/10; 606/13
(58) Field of Search ....................................... 606/3–19

(56) References Cited

U.S. PATENT DOCUMENTS 4,848,340 A   7/1989  Bille et al.
5,632,742 A * 5/1997  Frey et al. ................... 606/12

OTHER PUBLICATIONS

Written Opinion from PCT, Aug. 30, 2000, PCT.
Reply to PCT, Oct. 28, 2000, Applicant.

* cited by examiner

*Primary Examiner*—David M. Shay

(57) ABSTRACT

A method for tracking lateral movement of an object is disclosed employing a retro-reflective disk as a positioning reference and a simplified positioning detection to determine the position of the reference disk. The reference disk having a retro-reflective surface is affixed onto the object to be tracked. An illumination beam illuminates the reference disk from one direction and imaging optics forms a bright image spot of the reference disk with the backward scattering from the reference disk. A two-dimensional positioning detector detects the position of the bright image spot and an electronic circuit then generates positioning signals of the object for tracking applications. The bright image spot of the reference disk enables the use of single element two-dimensional positioning detector and thus enable fast detection (>1 kHz) of the object's position. An embodiment of the method on an eye-tracking system is described.

21 Claims, 3 Drawing Sheets

EYE TRACKING EMPLOYING A RETRO-REFLECTIVE DISK

REFERENCES

U.S. Patent Documents
  5,620,436 Lang and Clouts April 1997
    Method and apparatus for providing precise location of points on the eye
  5,632,742 Frey, et al May 1997
    Eye movement sensing method and system
  5,410,376 Cornsweet, et al April 1995
    Eye tracking method and apparatus
  5,430,505 Katz July 1995
    High speed eye tracking device and method
  5,345,281 Taboada, et al September 1994
    Eye tracking system and method This application claims the benefit of U.S. provisional application No. 60/093,618, filed on Jul. 21, 1998.

FIELD OF THE INVENTION

The present invention relates to an optical device for tracking lateral movement of an object. In particular, the present invention relates to an optical tracking device to track the eye movement during a laser surgery on the cornea.

BACKGROUND OF THE INVENTION

In a cornea surgery with a small laser beam, such as photo-refractive keratectomy or laser assisted in-situ keratomileuses, a fast and accurate eye tracking device is usually required to track the position of a patient's eye under surgery. With such a tracking device, the surgical laser beam can be delivered to predetermined positions on the eye even when the eye moves during the surgery. An example of this tracking device is described in U.S. Pat. No. 5,632,742 to Frey, et al. Another example is presented in U.S. Pat. No. 5,620,436 to Lang and Clouts.

These devices are optical systems operated in the infrared spectral range. To achieve a reliable eye tracking with high accuracy and high speed, it is essential to obtain on the cornea a well-defined reference of which the position can be determined precisely and quickly by an optical imaging system. Natural structures of the eye, such as the pupil and the limbus, do not always provide a reliable reference for this purpose. For instance, the centroid of the pupil moves when the pupil changes its size. In addition, these natural structures may be disturbed during the surgery.

High contrast masks have been proposed to apply onto the cornea to provide reliable references for a variety of eye-tracking devices. Frey et al. disclosed in U.S. Pat. No. 5,632,742 an ink ring affixed on the patient's eye. Lang and Clouts described in U.S. Pat. No. 5,620,436 a ring-shape aiming-fixture applied onto the patient's eye.

The main advantage of a ring shape mask is that it can be easily placed around the center of the cornea, where the laser surgery is taken place. On the other hand a ring shape mask is not convenient in many situations. One example is for laser assisted in-situ keratomileuses. In this type of surgery, a mechanical device called automated microkeratone laminates a thin layer of the cornea from the central part of the patient's eye. This layer is attached to the cornea by an uncut hinge and is flapped over to allow laser ablation on the corneal bed. This flap makes it difficult to apply a ring shape mask on the eye.

SUMMARY OF THE INVENTION

The present invention contemplates a small reference disk with a retro-reflective surface to enable fast and reliable tracking of lateral movement of an object such as an eye. The reference disk is affixed onto an object to be tracked. The disk has a retro-reflective surface to enhance significantly the backward scattering of an incident beam. An illumination beam illuminates the reference disk from a direction. An imaging optics collects the backward scattering to form a bright image spot of the reference disk. The lateral position of such a bright image spot can be detected by a single-element positioning-detector. An electronic circuit coupled to the positioning detector can then generate positioning signals of the reference disk and thus enable the tracking of the lateral movement of the object.

In the embodiments presented in this application, a retro-reflective disk and a single-element positioning-detector are implemented to provide fast eye tracking for refractive laser surgery on the cornea. In these embodiments, a retro-reflective disk of a few millimeters in diameter is affixed on the cornea near and outside the surgery area. An infrared light source located near the visual axis illuminates the eye and the reference disk from a working distance of about 25 cm. An imaging optics forms an image of the cornea area on a single-element positioning-detector. The strong backward scattering from the retro-reflective disk produces a bright spot in a basically dark background image. When the eye moves, the reference disk moves with the eye and the bright image spot moves on the positioning detector. An electronic circuit that reads in the output from the positioning detector generates positioning signals of the bright image spot and, thus, provides information on the eye movement. A control circuit can then use these positioning signals to control a beam steering mechanism to direct the surgical laser beam to follow the movement of the eye.

The reference disk may include a substrate and a retro-reflective surface according to one embodiment. The second surface of the disk is attachable to the cornea without slipping. The substrate can be made of paper or other materials, which are harmless to the cornea and durable for sterilization. The reference disk is preferably a disposable item.

The application of a retro-reflective reference disk simplifies the positioning detection of the eye to the positioning detection of a bright image spot. Consequently, single-element positioning-detector and simple electronics can be used to achieve fast and sensitive tracking of the eye movement. A prototype shows that positioning detection with a retro-reflective disk and a single-element positioning-detector can be faster than 10 kHz and sensitive to a few microns. In comparison, a CCD camera based positioning detection requires expensive frame grabber and sophisticate data-processing electronics. The up-date rate of a CCD camera is typically limited to 30 to 60 Hz. These and other aspects and advantages of the present invention will become more apparent in the following drawings, detailed description, and claims.

DETAILED DESCRIPTION OF THE PREFERRED EMBODIMENTS

Figure 1:
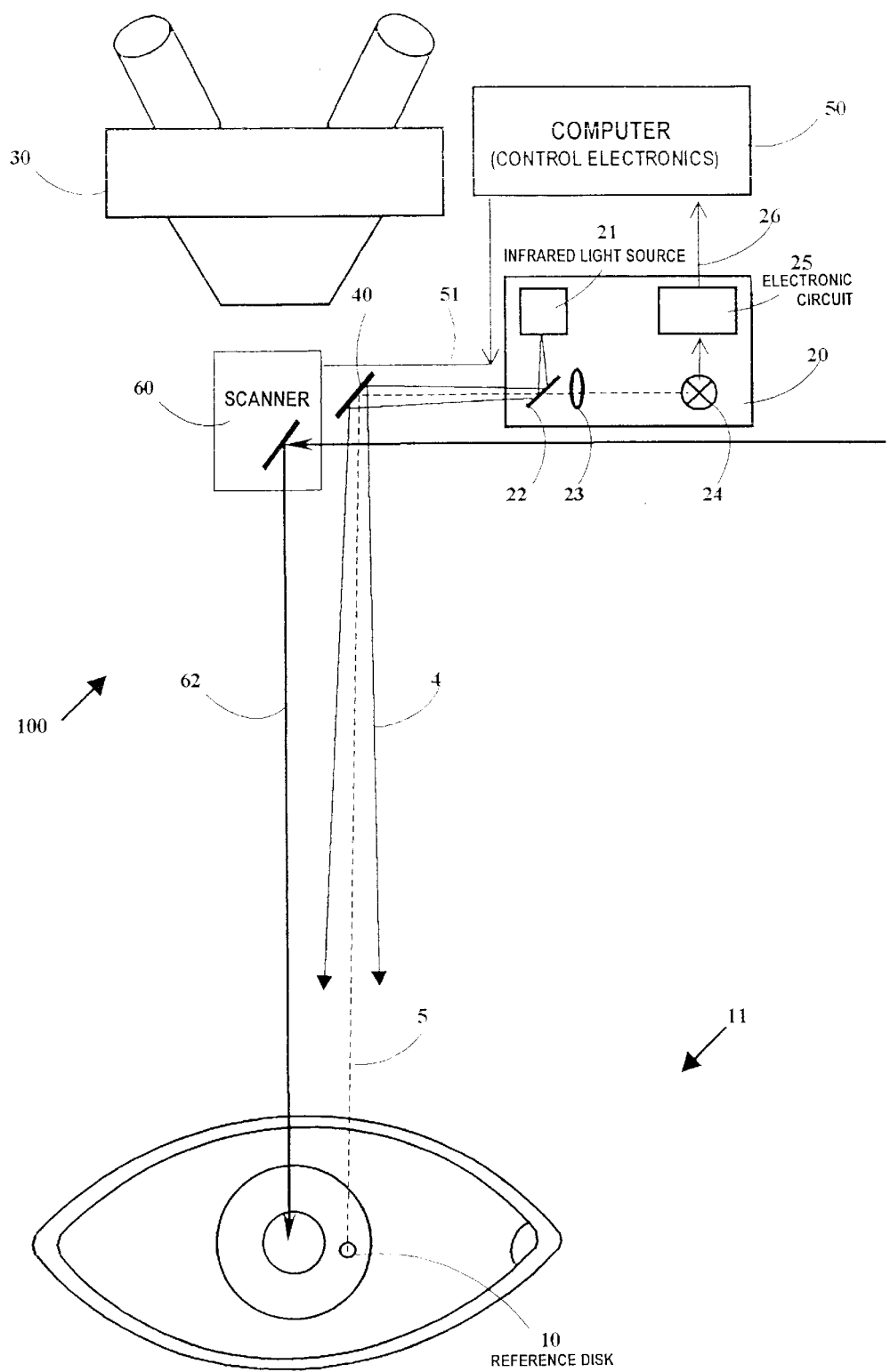
FIG. 1 is a schematic diagram showing one embodiment of an eye-tracking system in accordance with the present invention (open loop).

FIG. 1 is a schematic diagram showing one preferred embodiment of an eye-tracking system 100 in accordance with the present invention. The eye-tracking system 100 includes a position-detection device 20, control electronics 50, and a scanner 60.

To track the eye movement during a photo-refractive surgery, the tracking system 100 incorporates with a reference 10 affixed on the eye 11. The position-detection device 20 projects an infrared illumination beam 4 on the reference 10, detects the position of the reference 10, and thus detects any displacement of the subject's eye 11. Using the positioning signal 26 from the output of the position-detection device 20, the control electronics 50 controls the scanner 60 to steer a surgical laser beam 62 to follow the movement of the subject's eye 11.

The reference 10 is a retro-reflective disk with a diameter of a few millimeters. The reference disk 10 should be attached onto the cornea of the eye 11 and located near and outside the surgical area. Practically, the reference disk 10 can be attached onto the cornea simply by moisture. The reference disk 10 has a retro-reflective surface to enhance significantly the backward scattering of an illumination beam.

The position-detection device 20 consists of an infrared light source 21, a beam splitter 22, a focal lens 23, a single-element positioning-detector 24, and an electronic circuit 25. The position-detection device 20 and the other part of the tracking system 100 are located some 25 cm away from the patient's eye 11 so that enough working distance is available for the surgeon to handle the surgery.

The infrared light source 21 projects an infrared illumination beam 4 onto the eye 11 and the reference disk 10, via the beam splitter 22 and a turning mirror 40. This infrared light source 21 is preferably within the near infrared spectrum ranging from 750 nm to 1300 nm. The wavelength in this spectrum range is long enough to avoid-disturbing the surgeon and the patient and short enough for commonly available-photo-detector to have good responsibility. The intensity of the infrared illumination beam 4 on the eye 11 is preferably below 1 mW/cm$^2$ to avoid discomfort to the subject's eye 11.

A simple embodiment of an infrared light source 21 is a diffused laser beam from a laser diode operated around 800 nm. A diffuser may be used to reduce the spatial coherence of the laser beam to produce a more uniform and safer illumination beam on the eye. For an open-loop tracking system, the size of the illumination beam on the eye should be big enough to cover the desired tracking range.

The backward scattering 5 from the reference disk 10, as well as from the eye 11, traces backward into the position-detection device 20. This backward scattering beam 5 passes partially the beam splitter 22 and is then focused by the lens 23 to form an image onto the positioning detector 24. The image spot size of the reference disk 10 on the positioning detector 24 should be 1 mm or smaller for good spatial resolution of the disk position.

Because of the retro-reflective surface of the disk 10, the backward scattering from the disk 10 is many orders of magnitude stronger than that from the tissue of the eye 11. The image of the disk 10 on the positioning detector 24 is thus a bright spot over a basically dark background. The output signals from the positioning detector 24 are resolvable for the position of the bright spot and, consequently, can be used to determine the position of the reference disk 10. The electronic circuit 25 converts these output signals from the positioning detector 24 into positioning signals 26 of the centroid of the bright spot.

The control electronics 50 uses the positioning signals 26 as feedback to control the scanner 60 to follow the movement of the eye 11. The control electronics 50 can be either an analog circuit or a computer-based digital circuit. A digital circuit is discussed below, as it is preferable for its flexibility.

From the positioning signals 26 of the bright image spot, the computer 50 calculates the position of the reference disk 10 with a scale factor from calibration. An initial position of the disk 10 is registered and stored. A real time position of the disk 10 is then registered and compared with the initial position to determine the displacement of the disk 10. The computer 50 further then generates a signal 51 to drive the scanner 60 to deflect a surgical laser beam 62 to follow the movement of the eye 11.

It is the retro-reflective disk 10 leads to a bright spot to be formed on the image plane. Such an image of a bright spot over a basically dark background enables the use of the single-element positioning-detector 24 and a simple electronic circuit 25 to resolve the position of the patient's eye 11.

The tracking system 100 of FIG. 1 is an open-loop tracking system, in which only the surgical laser beam 62 follows the movement of the eye 11. In a close-loop tracking system, both the surgical laser beam 62 and the tracking illumination beam 4 follow the eye movement.

Figure 2:
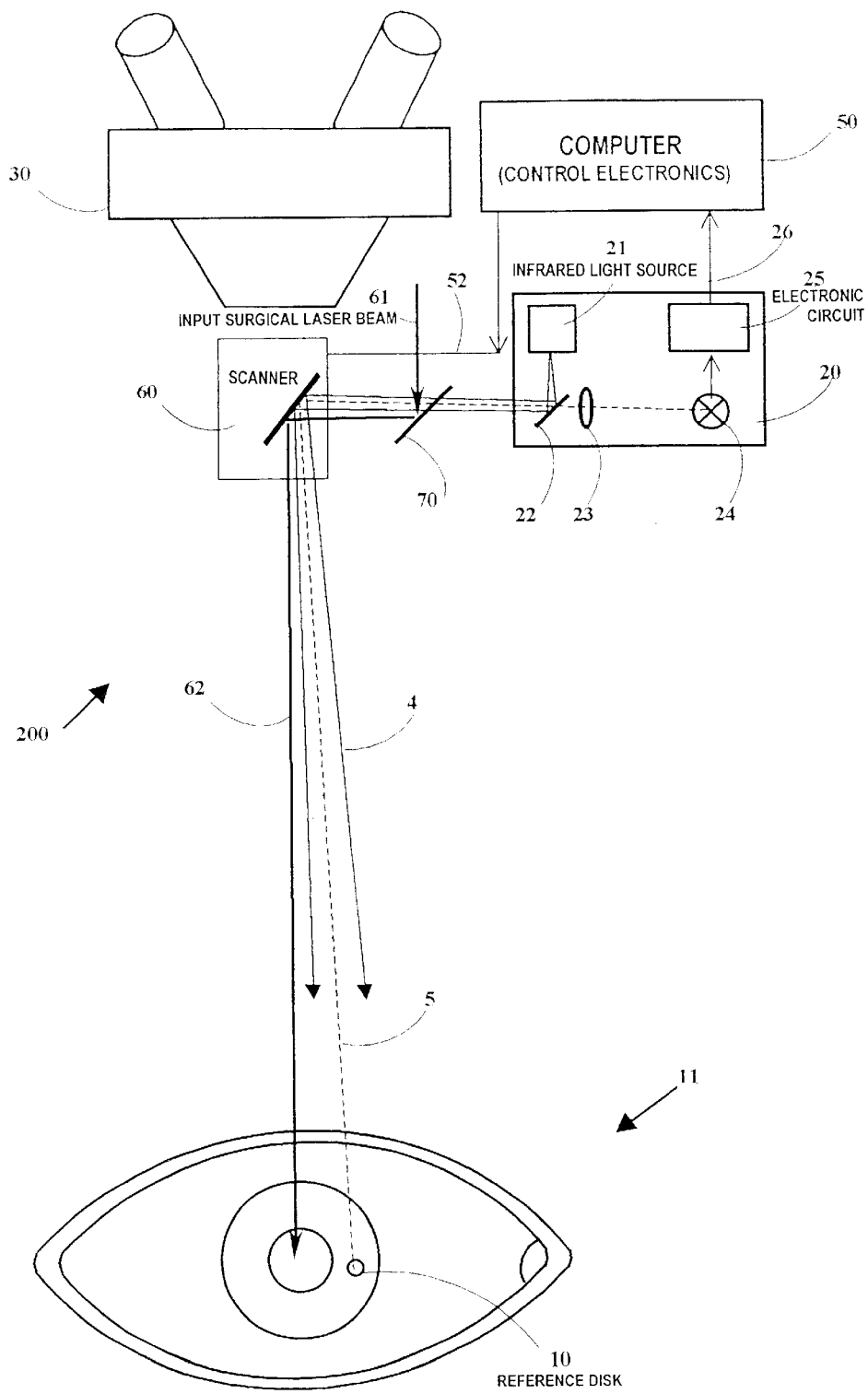
FIG. 2 shows another embodiment of an eye-tracking system in accordance with the present invention (closed loop).

FIG. 2 is a schematic diagram showing another preferred embodiment, a close-loop eye-tracking system 200, in accordance with the present invention. Similar to the embodiment of FIG. 1, this tracking system 200 includes a position-detection device 20, control electronics 50, and a scanner 60. Differently, the input surgical laser beam 61 and the infrared illumination beam 4 are combined through a diachronic mirror 70 and both reflect from scanner 60.

The backward scattering 5 from the disk 10 retraces back to the position-detection device 20 and forms a bright image spot on the single-element positioning detector 24. The electronic circuit 25 converts the output signals of the detector 24 into positioning signals 26 indicating the centroid of the bright image spot. These positioning signals 26, however, depend on not only the position of the disk 10 but also the angular position of the scanner 60.

To track the eye 11 with this close-loop tracking system 200, a computer 50 first registers and stores an initial position of the bright image spot. A real time position of the bright image spot is then registered and compared with its initial position to determine a displacement of the bright image spot on the positioning detector 24. This displacement is treated as an error signal. The computer 50 then generates a signal 52 to drive the scanner 60 to bring the error signal toward zero. This way the scanner 60 serves as a part of a negative-feedback servo loop to keep the bright image spot of the reference disk 10 stationary on the detector 24, while the disk 10 may move with the eye 11. A similar servo loop is described in U.S. Pat. No. 5,410,376 to Cornsweet et al., in which the pupil is used as a reference for tracking the eye movement. (The eye tracking device described there is not suitable for a photo-refractive surgery because it tracks the pupil and it needs to use an eyepiece in front of the eye. The beam pass to the pupil will be interrupted in a photo-refractive surgery and the eyepiece will interfere with the surgical laser beam.)

When the close-loop tracking is established, the eye 11 looks steady when it is viewed along the input surgical laser beam 61. The input surgical laser beam 61 is inserted by a diachronic mirror 70 into the scanner 60 and is then projected onto the eye 11 to serve as the surgical laser beam 62. The diachronic mirror 70 has a high reflectivity on the input surgical laser beam 61 and a high transmission to the infrared illumination beam 4. With the close-loop tracking, this input surgical laser beam 61 could be directed to any predetermined position on the eye as if the eye remains constant.

In either the tracking system 100 or 200, the real time position of the disk 10 can be registered at a high repetition rate so as to achieve fast response to the eye movement. For example, with a bright image spot of 1 $\mu$W, the single-element positioning detector 24 and the electronic circuit 25 can be easily operated faster than 500 Hertz, the speed required for tracking the involuntary eye movement. Detection speed higher than 10 kHz has been achieved with a prototype.

For a close loop tracking system 200, good linearity is not required and a quadrant detector can be used as the positioning detector 24. High-speed operation is also achievable with a quadrant detector.

If a CCD camera is used as a positioning detector 24, attention should be given to increase the readout speed of the camera. It is difficult to handle a readout rate of 500 Hertz from a two-dimensional CCD camera. To overcome this difficulty, the readout could be grouped into one sweep along x-direction and one sweep along y-direction. This way the two-dimensional CCD camera services as two orthogonal linear CCD cameras.

A high-speed scanner should be used for fast eye tracking. Galvanometer type scanners can have a good responsibility for small-step signal of 500 Hertz or higher. Fast scanners are commercially available from General Scanning Inc. or Cambridge Technology Inc.; both located in Watertown, Mass. Other type of beam steering mechanism may be used to replace the scanner 60 for various tracking requirements.

The eye-tracking system 100 or 200 is to incorporate into a laser surgical system to achieve more reliable and accurate surgical result. The tracking system is installed to track a patient's eye at a predetermined location and orientation relative to the surgical system. To operate, the surgeon should apply a retro-reflective disk 10 at a proper position on the patient's eye 11. Turn on the infrared light source 21 and the tracking system. Align the patient's eye 11 to the predetermined location and orientation (under a microscope 30, for instance). Activate the eye tracking and then start the laser surgery. Any eye movement during the surgery will be automatically compensated by the tracking system. The laser surgery can thus be performed on the eye as if the eye remains at its initial position.

The infrared light source 21 in FIG. 1 or 2 is for the tracking system only. In a surgical system, illumination for observation may be used. The illumination light for observation is in the visible spectrum range and can be decoupled from the tracking system by using optical filters.

Figure 3:
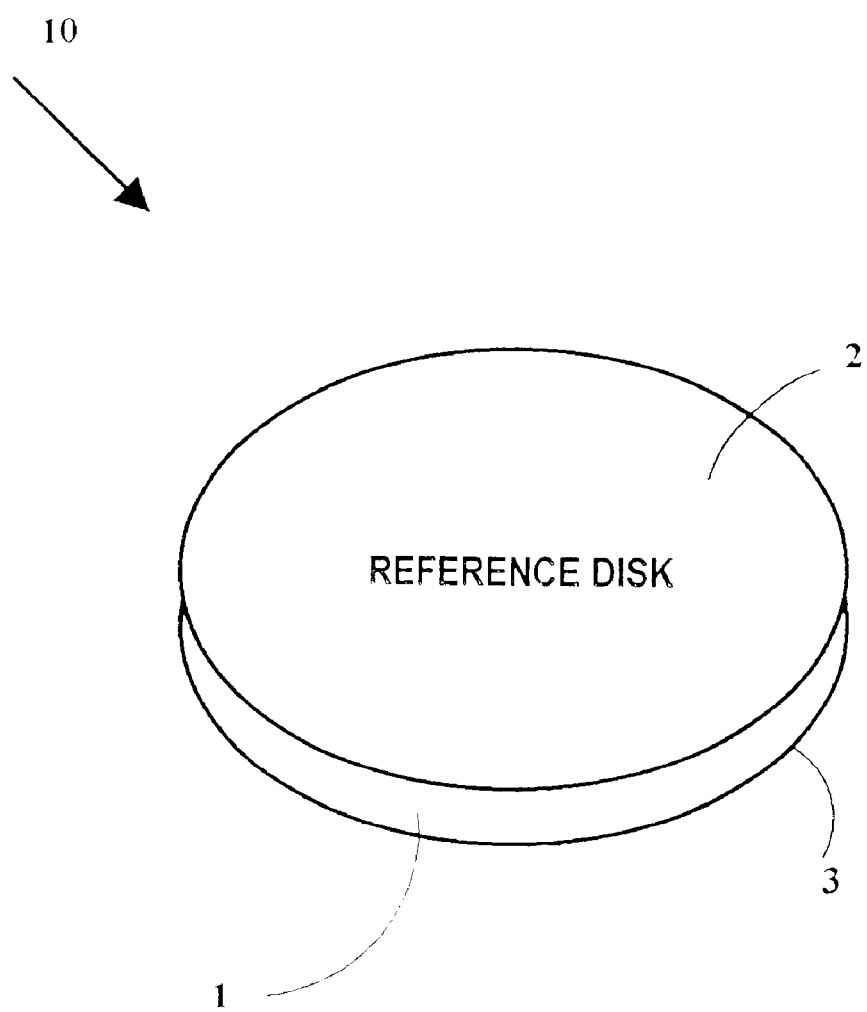
FIG. 3 is a schematic diagram of a reference disk with a retro-reflective surface.

FIG. 3 is a schematic diagram of a retro-reflective disk 10 in accordance with the present invention. The disk 10 consists of a substrate 1, a first surface 2, and a second surface 3.

The substrate 1 is made of paper or other materials, which are harmless to the cornea and are durable for sterilization. The substrate 1 should be light in weight. It has a diameter in the order of a few millimeters and a thickness of a fraction of the diameter.

The first surface 2 of the disk 10 is retro-reflective. The second surface 3 should be attachable to the cornea without slipping. Practically, the disk 10 can be attached on the cornea simply by moisture and can be removed easily after the surgery.

The retro-reflective surface 2 should have a strong backward scattering to incident illumination light. The backward scattering is much more condensed within a small cone angle around the incident illumination light. One way to produce a retro-reflective surface is to embed a large number of tiny glass or plastic spheres in a layer of paint and to make the spheres partially uncovered as the paint dries (S. R. Milk, Optics & Photonics News, December 1993, 6–7, Optical Society of America). These spheres should be transparent to the predetermined illumination light, preferable in the near infrared spectrum range for eye-tracking application. The paint should be oil-based and not degrade in water. It should also be durable for sterilizing. A practical substitute of this paint is to use a layer of reflective tape, available from hardware or auto-part stores.

The above figures and description are intended for illustrating the present invention. It is understood that various modifications can be made without departing from the scopes of the invention as defined in the appended claims.

What is claimed is:

1. A position-detection apparatus for tracking eye movement comprising:

a light source configured to produce a single infrared illumination beam projected onto an artificial reference affixed on an eye to be tracked, wherein said infrared illumination beam is projected near the visual axis of said eye and has a beam spot size on said eye greater than said reference and covering an area within which said reference moves with said eye, and wherein said reference has a retro-reflective surface producing backward scattering many orders of magnitude stronger than that from the tissue of said eye;

an optical collector configured and positioned at a distance from said eye to collect backward scattered infrared light from said reference to form a bright image spot of said reference at a selected image location, wherein said bright image spot appears at said selected image location over a substantially dark background;

a single-element positioning detector positioned at said selected image location to receive said bright image spot and configured to measure a two-dimensional position of said bright image spot of said reference on said positioning detector; and an electronic circuit coupled to said positioning detector to produce positioning signals indicative of a position of said reference according to a centroid of said bright image spot based on said measured two-dimensional position of said bright image spot on said positioning detector.

2. A position-detection apparatus as defined in claim 1 wherein said light source is configured to operate at a wavelength ranging from about 750 to about 1500 nm.

3. A position-detection apparatus as defined in claim 1 wherein said light source includes a laser diode.

4. A position-detection apparatus as defined in claim 1 wherein said a single-element positioning-detector is operable at a speed of 500 Hz or higher.

5. A position-detection apparatus as defined in claim 1, further comprising:

a surgical laser configured to produce a surgical laser beam; and a beam scanner positioned in an optical path of said surgical laser beam and configured to direct said surgical laser beam onto said eye for reshaping a cornea of said eye, wherein said electronic circuit is also coupled to control said beam scanner to follow movement of said eye.

6. A position-detection apparatus as defined in claim 5, wherein said beam scanner is not positioned to direct said infrared illumination beam to said eye.

7. A position-detection apparatus as defined in claim 5, wherein said beam scanner is also positioned in an optical path of said infrared illumination beam and hence to direct both said infrared illumination beam and said surgical laser beam onto said eye, and wherein said electronic circuit is configured to control said beam scanner to minimize a deviation of said position from a predetermined reference position for said bright image spot on said positioning detector.

8. A system, comprising:
   a surgical laser configured to produce a surgical laser beam for removing a tissue of an eye located at a selected position;
   a surgical beam scanner positioned in an optical path of said surgical laser beam to control and direct said surgical laser beam to a surgical area on the eye;
   a reflector configured to attach to the eye outside the surgical area to move with the eye and having a retro-reflective surface producing backward scattering many orders of magnitude stronger than that from the tissue of said eye;
   an illumination source configured to produce a single infrared illumination beam projected near the visual axis onto the eye with a beam size greater than said reflector to illuminate at least an area within which said reflector moves with the eye;
   an optical collector configured and positioned to collect backward scattered infrared light from said reflector to form a bright image spot of said reflector at a selected image location, wherein said bright image spot appears at said selected image location over a substantially dark background;
   a single-element positioning detector positioned at said selected image location to receive said bright image spot and configured to measure a two-dimensional position of said bright image spot of said reflector on said positioning detector; and
   an electronic circuit coupled to said positioning detector to produce positioning signals indicative of a position of said reflector according to a centroid of said bright image spot based on said measured two-dimensional position of said bright image spot on said positioning detector, said electronic circuit operable to control said surgical beam scanner to track movement of the eye according to said position of said reflector.

9. The system as in claim 8, wherein said beam scanner is not positioned to direct said infrared illumination beam to the eye.

10. The system as in claim 8, wherein said surgical beam scanner is also positioned in an optical path of said infrared illumination beam and hence to direct both said infrared illumination beam and said surgical laser beam onto the eye, and wherein said electronic circuit is configured to control said surgical beam scanner to minimize a deviation of said position from a predetermined reference position for said bright image spot on said positioning detector.

11. The system as in claim 8, wherein said single-element positioning detector is operable at a speed of 500 Hz or higher.

12. The system as in claim 8 wherein said reflector includes:
   a substrate made from a material harmless to human corneas and durable for sterilizing;
   a first surface having a retro-reflective coating operable at infrared illumination light; and
   a second surface attachable onto a human cornea.

13. The system as in claim 12 wherein said substrate is made of materials including paper and plastic.

14. The system as in claim 12, wherein said retro-reflective coating is formed by a layer of a reflective tape.

15. A method for tracking eye movement comprising the steps of:
   affixing onto an eye a reference having an artificial retro-reflective surface producing backward scattering many orders of magnitude stronger than that from the tissue of said eye;
   projecting near the visual axis of said eye an infrared illumination beam onto said reference;
   controlling said infrared illumination beam to have a beam size at said eye to cover an area in which said reference moves with said eye;
   collecting backward scattered illumination light from said reference to form a bright image spot of said reference over a substantially dark background;
   using a single-element positioning detector to receive said bright image spot and to detect a two-dimensional position of said bright image spot of said reference on said positioning detector;
   causing a centroid of said bright image spot to be obtained to represent a position of said reference and hence said eye based on said two-dimensional position on said positioning detector; and
   using said position to control a surgical laser beam directed onto said eye so as to follow movement of said eye.

16. A method as defined in claim 15, further comprising:
   using a common beam scanner to direct both said infrared illumination beam and said surgical laser beam onto said eye; and
   controlling said common beam scanner to minimize a deviation of said position from a predetermined reference position for said bright image spot on said positioning detector.

17. A method as defined in claim 15, further comprising:
   using a surgical beam scanner to control and direct said surgical laser beam onto said eye independently from directing said infrared illumination beam; and
   controlling said surgical beam scanner to direct said surgical laser beam in a way to correct an effect on a relative positioning of said surgical laser beam on said eye caused by movement of said eye.

18. A method for tracking lateral movement of an object comprising the steps of:
   affixing onto the object an artificial reference having a retro-reflective surface producing backward scattering many orders of magnitude stronger than that from said object;
   projecting an illumination beam from a predetermined direction onto said reference;
   controlling said infrared illumination beam to have a beam size at said object to cover said reference and an area within which said reference moves with said object;

providing an optical means to collect backward scattered light from said reference to form a bright image spot of said reference over a substantially dark background;

providing a single-element, two-dimensional positioning detector to detect the position of said bright image spot of said reference;

providing an electronic circuit coupled to said two-dimensional positioning detector to produce positioning signals of said object according to a centroid of said bright image spot; and using said positioning signals to track movement of said object.

19. A method as defined in claim 18 further comprising using a light source to produce said illumination beam at a wavelength range from 300 to 1500 nm.

20. A method as defined in claim 18, further comprising:

directing a second light beam onto said object;

using a beam scanner to control and direct said second light beam onto said object independently from directing said infrared illumination beam; and controlling said beam scanner to direct said second light beam in a way to correct an effect on a relative positioning of said second light beam on said object caused by movement of said object.

21. A method as defined in claim 18, further comprising:

directing a second light beam onto said object;

using a common beam scanner to direct both said infrared illumination beam and said second light beam onto said object; and controlling said common beam scanner to minimize a deviation of said position from a predetermined reference position for said bright image spot on said positioning detector.

* * * * *